United States Patent [19]

Mansell et al.

[11] Patent Number: 5,731,482
[45] Date of Patent: Mar. 24, 1998

[54] METHOD FOR PURIFYING PERCHLOROETHYLENE CONTAINING DICHLOROBUTADIENE

[75] Inventors: J. Douglas Mansell; Robert K. Pertuit, both of Sulphur; J. Boyd Alleman, Lake Charles, all of La.; W. Eugene Wimer, Delmont, Pa.

[73] Assignee: PPG Industries, Inc., Pittsburgh, Pa.

[21] Appl. No.: 778,932

[22] Filed: Jan. 3, 1997

[51] Int. Cl.$^6$ ............................ C07C 17/38; C07B 63/00
[52] U.S. Cl. ............................ 570/238; 204/158.21
[58] Field of Search ........................ 204/158.21; 570/238

[56] References Cited

U.S. PATENT DOCUMENTS

| | | |
|---|---|---|
| 2,914,576 | 11/1959 | Vancamp et al. |
| 2,951,103 | 8/1960 | Ellsworth et al. |
| 2,979,540 | 4/1961 | Asadorian et al. |
| 3,449,450 | 6/1969 | Bohl et al. |
| 3,480,534 | 11/1969 | Harmer et al. |
| 4,028,426 | 6/1977 | Mansell |
| 5,077,440 | 12/1991 | Zviely et al. |
| 5,306,740 | 4/1994 | Las et al. |

FOREIGN PATENT DOCUMENTS

| | | |
|---|---|---|
| 1 406 502 | 9/1975 | United Kingdom |
| 2 224 026 | 4/1990 | United Kingdom |

*Primary Examiner*—Alan Siegel
*Attorney, Agent, or Firm*—Irwin M. Stein

[57] ABSTRACT

Perchloroethylene containing contaminating amounts of dichlorobutadiene is treated with bromine, e.g., elemental bromine, in the presence of a free-radical initiator, thereby to produce perchloroethylene substantially-free of dichlorobutadiene and without significant loss of perchloroethylene. A bromine scavenger, e.g., trichloroethylene, can be added to the treated perchloroethylene to react with excess bromine that may be present in the perchloroethylene.

16 Claims, No Drawings

METHOD FOR PURIFYING PERCHLOROETHYLENE CONTAINING DICHLOROBUTADIENE

DESCRIPTION OF THE INVENTION

Perchloroethylene, i.e. tetrachloroethylene(CAS No. 127-18-4), is an ethylenically unsaturated two carbon compound containing four chlorine atoms. It is the most stable of the chlorinated ethylenes and ethanes, having no flash point and requiring only minor amounts of stabilizers. These two properties combined with its excellent solvent properties account for its use in the dry-cleaning industry, metal cleaning and vapor degreasing. It is also used as an intermediate in the manufacture of hydrochlorofluorocarbons and hydrofluorocarbons.

Many processes have been used to produce perchloroethylene. For example, it can be produced by the noncatalytic chlorination of ethylene dichloride or other two carbon chlorinated hydrocarbons; by the reaction of ethylene dichloride with chlorine or hydrogen chloride and oxygen in the presence of a catalyst; by the catalytic reaction of tetrachloroethane and oxygen at elevated temperatures (U.S. Pat. No. 2,952,103); by a two-step process involving the vapor phase chlorination of 1,2-dichloroethane followed by the vapor phase catalytic oxychlorination of the product of the first step (U.S. Pat. No. 3,449,450); or by the catalytic reaction of mixtures of 1,1,2-trichloroethane, and symmetrical and unsymmetrical tetrachloroethane with hydrogen chloride and oxygen.

Perchloroethylene, as produced, is usually separated from other product and by-product chlorinated compounds, e.g. trichloroethylene, by distillation. However, due to physical limitations of the distillation equipment available and/or the closeness of the boiling points of some by-product chlorinated compounds, separation of substantially pure perchloroethylene from such by-products is difficult to achieve. For example, certain dichlorobutadiene compounds present in perchloroethylene product cannot be easily separated from perchloroethylene by distillation. Substantially pure perchloroethylene is required for some commercial applications. Therefore, perchloroethylene that is substantially free of contaminating amounts of dichlorobutadiene is desirable.

It has now been discovered that perchloroethylene containing contaminating amounts of dichlorobutadiene can be treated with bromine, e.g., elemental bromine, thereby to produce brominated dichlorobutadiene, which can be separated readily from perchloroethylene. Preferably, the treatment is conducted in the presence of a free-radical initiator, e.g., light and/or an organic free radical initiator. In a further embodiment, an organic material that reacts more readily with bromine than perchloroethylene can be added to the treated perchloroethylene to react with any excess bromine present, thereby removing bromine reactant from the treated perchloroethylene.

DETAILED DESCRIPTION OF THE INVENTION

Chlorinated butadienes have been found to be present in commercially produced perchloroethylene. For some industrial applications, perchloroethylene substantially-free of such chlorinated butadienes is required. The particular chlorinated butadienes that may be present in perchloroethylene will vary depending on the process and starting materials used to produce the perchloroethylene product. Examples of 1,3- and 1,2-dichlorobutadiene compounds that may be present include compounds such as 1,1-dichloro-1,3-butadiene, 1,2-dichloro-1,3-butadiene, 2,3-dichloro-1,3-butadiene-1,4-dichloro, 1,3-butadiene, 1,1-dichloro-1,2butadiene, 1,3-dichloro-1,2-butadiene, 1,4-dichloro-1,2butadiene, 4,4-dichloro-1,2-butadiene, 3,4-dichloro-1,2butadiene and mixtures of such chlorinated butadienes. Other organic compounds with identical masses such as dichlorocyclobutene, methyl-dichlorocyclopropene and methylene-dichloro-cyclopropane may also be present.

The amount of chlorinated butadienes, e.g., dichlorobutadiene, present in the perchloroethylene subjected to the process of the present invention is typically less than 1000 parts per million (ppm). More typically, the amount of chlorinated butadienes present in the perchloroethylene is less than 500 ppm, more typically less than 200 ppm. The aforedescribed amounts of chlorinated butadienes, e.g., dichlorobutadienes, are referred to herein as contaminating amounts.

In accordance with the present invention, perchloroethylene containing contaminating amounts of chlorinated butadienes is contacted with bromine in amounts sufficient to react with the chlorinated butadiene contaminants to produce materials, e.g., bromine-containing chlorinated butenes, that have a boiling point sufficiently higher than perchloroethylene to permit their separation by distillation. While elemental bromine is the preferred source of bromine used to react with the chlorinated butadienes, it is contemplated that other sources of bromine, e.g., interhalogen compounds such as bromine chloride, which will liberate bromine under the conditions at which the method of the present invention is performed may also be used.

The amount of bromine used in accordance with the method of the present invention is at least a stoichiometric amount, e.g., an equal molar amount, based on the amount of chlorinated butadienes present in the perchloroethylene. Commonly, a slight excess of bromine is used in order to achieve complete reaction of the chlorinated butadienes and other unsaturated organic compounds of similar mass with bromine. Too high an excess of bromine is to be avoided because bromine itself is a contaminant and, as discussed hereinafter, is removed by the addition of an organic bromine scavenger compound. The mole ratio of bromine to chlorinated butadienes will range from 1:1 to 50:1, preferably from 1:1 to 10:1, more preferably from 1.5:1 to 2:1.

Although perchloroethylene is an ethylenically unsaturated chlorinated two carbon compound, it has been found surprisingly that bromine reacts very slowly with perchloroethylene under the conditions of the present method, vis-a-vis, the chlorinated butadienes. It has been observed that the chlorinated butadienes, e.g., dichlorobutadiene, react with bromine substantially faster than perchloroethylene; and, therefore the reaction of bromine with the chlorinated butadiene contaminant can be carried out in the presence of perchloroethylene without a substantial loss of perchloroethylene due to its reaction with bromine.

In a preferred embodiment, treatment of perchloroethylene containing contaminating amounts of chlorinated butadienes is conducted in a suitable reactor or reaction zone in the presence of a free-radical initiator. The free-radical initiator can be an organic free-radical initiator or a source of light, e.g., light from a tungsten halogen lamp.

Examples of organic free radical initiators include:
2,2'-azobis(2-methylpropanenitrile), known commercially as azobisisobutyronitrile, [CAS 78-67-1],
2,2'-azobis(2-methylbutanenitrile) [CAS 13472-08-7],
2,2'-azobis(2,4-dimethylpentanenitrile) [CAS 4419-11-8],
2,2'-azobis(4-methoxy-2,4-dimethylpentanenitrile) [CAS 15545-97-8], 1,1'-azobis(cyclohexanecarbonitrile) [CAS 2094-98-6],
4,4'-azobis(4-cyanopentanoic acid) [CAS 2638-94-0],
2,2'-azobis(2-methylpentanenitrile),
22'-azobis(2-methylhexanenitrile),
2,2'-azobis(2,3-dimethylpentanenitrile),
2,2'-azobis(2,3,3-trimethylbutanenitrile),
2,2'-azobis(2,4,4-trimethylpentanenitrile),
2,2'-azobis(2-methyl-3-phenylpropanenitrile),
2,2'-azobis(2-cyclohexylpropanenitrile),
1,1'-azobis(cycloheptanecarbonitrile),
1,1-azobis(cyclooctanecarbonitrile),
1,1-azobis(cyclodecanecarbonitrile),
2-(tert-butylazo)-4-methoxy-2,4-dimethylpentanenitrile [CAS 55912-17-9],
2-(tert-butylazo)-2-methylpropanenitrile [CAS 25149-46-6],
2-(tert-butylazo)-2-methylbutanenitrile [CAS 52235-20-8],
1-(tert-amylazo)cyclohexanecarbonitrile [CAS 55912-19-1],
1-(tert-butylazo)cyclohexanecarbonitrile [CAS 25149-47-7],
2-[(1-chloro-1-phenylethyl)azo]-2-phenylpropanenitrile diisopropylperoxydicarbonate [CAS 105-64-6],
di-sec-butyl peroxydicarbonate,
di-n-propyl peroxydicarbonate [CAS 16066-38-9],
di-(2-ethylhexyl) peroxydicarbonate,
dicyclohexyl peroxydicarbonate, [CAS 1561-49-5], and mixtures of such organic free radical initiators. Other examples of organic free radical initiators are given in *Kirk-Othmer Encyclopedia* of Technology, third edition, volume 17, pages 1-90 (1982), which disclosure is hereby incorporated by reference.

As the source of initiating light, there can be mentioned light from a tungsten halogen lamp, sunlight or light from mercury vapor lamps. It is contemplated that organic free radical initiators can be used in combination with a source of initiating light.

The amount of free-radical initiator used is that amount which enhances the rate of reaction of the chlorinated butadiene with the bromine reactant, i.e., an initiating amount. In the case of the organic-free-radical initiator, between 0.0001 and 0.02 weight percent, basis the amount of perchloroethylene (1–200 ppm) is typically used. More typically, from 0.0002 to 0.01 weight percent of organic-free radical initiator, based on the amount of perchloroethylene, (2–100 ppm) is used.

In the case of the initiator light source, any source of light, e.g., sunlight, or light from a tungsten halogen lamp or mercury vapor lamp, which is sufficient to enhance the rate of reaction between bromine and the chlorinated butadienes can be used. It is postulated that such light provides bromine free radicals which react with the chlorinated butadienes. Light having a wave length in the range of from the near ultraviolet to the mid visible range, e.g., from 3000 to 5000 Angstroms, more particularly, 3500 to 4500 Angstroms, is particularly contemplated. The effectiveness of a light source as a free-radical initiator in the method of the present invention can be assessed readily by its ability to cause the disappearance of the bromine color present in perchloroethylene to which bromine has been added. The more rapidly the bromine color disappears in the reaction medium, the more effective the free-radical initiator.

Mixing of perchloroethylene containing contaminating amounts of chlorinated butadienes with the source of bromine is conducted in any suitable reactor or reaction zone, which may or may not have an initiating light source. A suitable reactor may be a glass pipe that is sufficiently transparent to admit light from the source of initiating light; a Teflon® polytetrafluoroethylene reaction zone, which admits light through its walls; piping with an internally mounted initiating light source; or a tank reactor with an internally mounted initiating light source. A tank reactor may contain a stirrer and may be used to increase the retention time between the bromine and the chlorinated butadienes present in the perchloroethylene.

In the case of the organic free-radical initiator, such initiator may be introduced into the perchloroethylene stream at the point at which bromine is introduced into the perchloroethylene stream; or in the case of a tank reactor, the organic free-radical initiator may be charged directly to the tank reactor. It is contemplated that the organic-free radical initiator may be used in combination with an initiator light source.

Typically, the source of bromine, e.g., elemental bromine, is introduced into liquid perchloroethylene containing contaminating amounts of chlorinated butadiene prior to or within the reaction or contact zone where the two are mixed intimately. In a preferred embodiment, the bromine and liquid perchloroethylene are premixed in the absence of the free radical initiator (light or organic free radical initiator) and then charged to the reaction zone and into contact with the initiator, i.e., light or the organic free radical initiator. This procedure results in a more efficient use of the bromine. For example, when the reaction zone is within a glass pipe (either with an internally mounted or externally mounted light source), liquid contaminated perchloroethylene is introduced into the glass pipe and liquid bromine is introduced into the perchloroethylene downstream of the reaction zone. The liquid bromine is introduced at a pressure sufficient to overcome the system pressure of the liquid perchloroethylene as it flows through the glass pipe. A static mixer may be used to mix the perchloroethylene and bromine prior to the reaction zone to avoid localized reactions of the bromine.

The reaction between bromine and chlorinated butadienes will typically be conducted at temperatures of from 50° F. (10° C.) to 250° F. (121° C.) and at system pressures. In commercial practice, the method of the present invention is conducted with a liquid perchloroethylene process stream, which is at a pressure above atmospheric.

Typically, the retention time required for the substantial reaction of the chlorinated butadienes, e.g., dichlorobutadiene, with bromine at temperatures of from 50° F. (10° C.) to 250° F. (121° C.) are on the order of from 0.5 to 45 minutes, e.g., 2 to 20 or 30 minutes. However, as mentioned, a tank reactor may be used to increase retention time, if required.

While not wishing to be bound by any particular theory, it is believed that bromine reacts more readily with the chlorinated butadiene compounds in the perchloroethylene to produce dibromodichlorobutenes, which have a boiling range sufficiently higher than perchloroethylene to allow the separation and recovery of substantially pure perchloroethylene by conventional distillation means. The perchloroethylene recovered in accordance with the method of the present invention typically contains less than 10 ppm chlorinated butadiene, as determined by mass spectrometry. Such perchloroethylene is considered to be substantially-free of chlorinated butadienes. Contaminated perchloroethylene treated in accordance with the process of the present invention has resulted in the recovery of perchloroethylene having an average 5 to 8 ppm, e.g., 6.5 ppm, dichlorobutadienes. It is believed that the process of the present invention results in perchloroethylene containing less than 5 ppm dichlorobutadiene, but that dehalogenation of the dibromodichlorobutenes during distillation of the treated perchloroethylene causes regeneration of some dichlorobutadiene.

In accordance with a further embodiment of the present invention, an organic compound that reacts readily with bromine and which (in its original or brominated state) can be separated by distillation from perchloroethylene is added to the treated contaminated perchloroethylene downstream from the reaction zone. The addition of such a material serves to remove excess bromine from the treated perchloroethylene stream, thereby to produce a perchloroethylene substantially free of bromine. To avoid a significant loss of perchloroethylene, the organic compound added as the bromine acceptor (scavenger) reacts more readily and preferentially with bromine than does perchloroethylene, i.e., the rate of reaction of bromine with the organic acceptor is significantly higher than the rate of reaction of bromine with perchloroethylene.

Typically, the organic compound added is a monoethylenically unsaturated material, e.g., a monoethylenically unsaturated chlorinated material such as a chlorinated ethylene, e.g., trichloroethylene such as 1,1,2-trichloroethylene. The amount of such material added to the treated perchloroethylene stream is an amount sufficient to react with substantially all of the excess bromine present in the treated perchloroethylene stream and will typically be between 0.1 and 2.0 weight percent, based on the amount of perchloroethylene.

Other organic compounds capable of reacting with bromine in the perchloroethylene stream that may be added to the treated perchloroethylene as a bromine acceptor include: cis-1,2-dichloroethylene, trans-1,2-dichloroethylene, 1,1-dichloroethylene, acetylene, ethylene, decene, ethylenically unsaturated polymers of butadiene, beta carotene or heavy aromatic naphtha. As indicated, the organic compound added to combine or scavenge the excess bromine in the perchloroethylene stream should be a compound which is readily separated from the perchloroethylene by distillation. The brominated derivatives of said scavenger compound should also be readily separable from perchloroethylene by distillation.

Perchloroethylene boils at 121° C., at 101 kPa. In order to separate perchloroethylene from higher boiling materials, it is preferred that such higher boiling materials have a boiling point of at least 10° C. greater than perchloroethylene in order to be readily removable by conventional distillation columns in current commercial use in the production of perchloroethylene. In order to separate perchloroethylene from lower boiling materials, it is preferred that such lower boiling materials have a boiling point of at least 10° C. less than perchloroethylene in order to be readily removable by conventional distillation columns in current commercial use in the production of perchloroethylene.

Other than in the operating examples, or where otherwise indicated, all numbers expressing quantities of components or reaction conditions used herein are to be understood as modified in all instances by the term "about". As used in the description, examples and claims, all percents and parts are by weight unless otherwise specifically indicated.

The present invention is more particularly described in the following examples which are intended as illustrative only, since numerous modifications and variations therein will be apparent to those skilled in the art.

EXAMPLE 1

Perchloroethylene [25 milliliters (ml)] containing dichlorobutadiene in concentrations detectable by gas chromatography using a mass-spectrometer as a detector was charged to a thin Pyrex vial. A drop of bromine was added to the perchloroethylene, the vial capped and the contents in the vial exposed to sunlight for several minutes. When the bromine color in the vial had faded, the sample was analyzed by gas chromatography using a mass spectrometer as detector. No dichlorobutadiene was detected.

EXAMPLE 2

The process of Example 1 was repeated except that the vial was exposed to light from a tungsten halogen lamp (Osram 120 v, 500 watt, C438). After the bromine color had faded, the sample was analyzed and no dichlorobutadiene was detected.

EXAMPLE 3

The process of Example 1 was repeated except that the capped vial was placed in a quartz tube, the exterior annulus of which was filled with perchloroethylene. The sample in the vial was exposed to light from a tungsten-halogen lamp (Osram 120 v, 500 watt, C438) which light passed through the perchloroethylene in the annulus of the quartz tube. After the bromine color had faded, the sample was analyzed and no dichlorobutadiene was detected.

EXAMPLE 4

Perchloroethylene containing dichlorobutadiene was charged to 21 feet of 1/4 inch (0.64 cm) outside diameter Teflon® tubing at a rate of 40 ml/minute. The tube was wound around a pipe and was illuminated on one side with a 500 watt tungsten-halogen lamp Osram 120 v, 500 watt, C438). Liquid bromine was added continuously to the perchloroethylene stream using a syringe pump to give a solution concentration of bromine in perchloroethylene of 67 parts per million (ppm). A short section near the bromine injection point was shielded from light to allow better mixing of the bromine with the perchloroethylene before the stream passed into the section of the tubing exposed to light. The reduction found in dichlorobutadiene concentration compared to incoming dichlorobutadiene-containing perchloroethylene was 95 percent, as determined by the ratio of peak areas from analyses performed by gas chromatography using a mass spectrometer as detector.

EXAMPLE 5

To a stream of perchloroethylene [18.5 gallons/minute (gpm)] containing a contaminating level of dichlorobutadiene (585 ppm) was added liquid bromine (16 lbs/hr) in the dark. The liquid bromine was injected directly into the perchloroethylene stream at a pressure sufficient to overcome the process stream pressure. The flow rate was controlled by adjusting a metering valve. The bromine feed vessel sat on a load cell to give weight averages of the feed rate. The stream containing bromine was passed through a static mixer before entering the reaction zone which was a Pyrex glass pipe [6 inch (15.2 cm) inner diameter by 214.5 feet long [65.4 meter (m)]. The pipe was hung from the walls of a rectangular box, which acted as a secondary container in case of leaks or glass failure. The pipe containing the process stream entered the glass pipe near the floor of the rectangular enclosure and was wound inside the enclosure by adjusting the angles at the corners to create a rectangular along the length of the reactor and exit instead of accumulating. At a point 52 feet (15.9 m) from the downstream end of the reactor a stream of trichloroethylene (0.2 gpm) was added to react with any excess bromine. A static mixer followed the addition point of trichloroethylene. Illumination of the reactor was provided by 24 General Electric 400 watt mercury vapor lamps (HR400A33) arranged in rows on the ceiling of the rectangular enclosure. The stream exited the glass reactor and passed to a small surge vessel. The stream was then routed to two distillation columns. The first column removed components lighter than perchloroethylene and the second removed components heavier than perchloroethylene, including brominated chlorinated butadiene. The perchloroethylene overhead product from the second column contained 6.1 ppm of dichlorobutadiene, as determined by gas chromatography using a mass spectrometer as detector.

EXAMPLE 6

To a stream of perchloroethylene (15.6 gpm) containing a contaminating level of dichlorobutadiene (97.6 ppm) was added liquid bromine (3.7 lbs/hr) in the dark. The liquid bromine was injected directly into the perchloroethylene stream at a pressure sufficient to overcome the process stream pressure. The flow rate was controlled by a metering valve. The bromine feed vessel was set on a load cell to give longer term weight change base averages of the feed rate. The stream containing bromine was passed through a static mixer before entering the reaction zone described in Example 5. At 52 feet (15.9 m) from the end of the reactor, a stream of trichloroethylene (0.16 gpm) was added to react with any excess bromine. A static mixer followed the addition point of trichloroethylene. Illumination of the reactor was provided by 24 mercury vapor lamps as described in Example 5. The stream exited the glass reactor and passed to a small surge vessel. The perchloroethylene stream contained <1 ppm dichlorobutadiene, as determined by gas chromatography using a mass spectrometer as detector. Following distillation in the two distillation columns described in Example 5, the level of dichlorobutadiene in the perchloroethylene overhead product stream was found to be 4.7 ppm, as determined by gas chromatography using a mass spectrometer as detector.

Although the present invention has been described with reference to the specific details of particular embodiments thereof, it is not intended that such details be regarded to limit the scope of the invention except in so far as and to the extent that they are included in the accompanying claims.

What is claimed is:

1. A method of purifying perchloroethylene containing contaminating amounts of chlorinated butadiene, comprising treating said contaminated perchloroethylene with bromine in the presence of a free-radical initiator, and thereafter recovering thus treated perchloroethylene.

2. The method of claim 1 wherein the chlorinated butadiene is present in amounts of less than 1000 ppm.

3. The method of claim 2 wherein the chlorinated butadiene is dichlorobutadiene.

4. The method of claim 1 wherein the free radical initiator is an organic free radial initiator or a source of initiating light.

5. The method of claim 4 wherein the organic free radical initiator is azobisisobutyronitrile.

6. The method of claim 1 wherein the mole ratio of bromine to chlorinated butadiene is from 1:1 to 50:1.

7. The method of claim 1 wherein said bromine treated perchloroethylene is subsequently contacted with an organic bromine acceptor.

8. The method of claim 7 wherein the bromine acceptor is trichloroethylene.

9. The method of claim 8 wherein the amount of trichloroethylene used is from 0.1 to 2.0 weight percent, based on the amount of perchloroethylene.

10. A method of purifying a liquid stream of perchloroethylene containing contaminating amounts of chlorinated butadiene, comprising adding bromine to said liquid perchloroethylene in amounts sufficient to combine with substantially all of the chlorinated butadiene in the perchloroethylene stream in a reaction zone and in the presence of a free radial initiator, and recovering perchloroethylene containing less than 10 ppm chlorinated butadiene.

11. The method of claim 10 wherein the free radical initiator is selected from light, organic free-radical initiators and a combination of light and organic free radical initiator.

12. The method of claim 11 wherein the source of light is sunlight, tungsten halogen lamps or mercury vapor lamps.

13. The method of claim 12 wherein the wave lengths of the light source is in the range of from the near ultraviolet to the mid-visible.

14. The method of claim 10 wherein the amount of chlorinated butadiene present in the contaminated perchloroethylene is less than 1000 ppm, the mole ratio of bromine to dichlorobutadiene is from 1:1 to 10:1 and the free radical initiator is light.

15. The method of claim 14 wherein an organic bromine acceptor compound is added to the bromine-treated perchloroethylene stream, said organic compound and its brominated derivatives being capable of being separated from perchloroethylene by distillation.

16. The method of claim 15 wherein the organic compound is trichloroethylene.

* * * * *